US012648808B2

(12) United States Patent (10) Patent No.: US 12,648,808 B2
Okarski (45) Date of Patent: Jun. 9, 2026

(54) IRRIGATION TUBING WITH REGULATED FLUID EMISSION

(71) Applicant: Biosense Webster (Israel) Ltd., Yokneam (IL)

(72) Inventor: Kevin M. Okarski, Monrovia, CA (US)

(73) Assignee: Biosense Webster (Israel) Ltd. (IL)

( * ) Notice: Subject to any disclaimer, the term of this patent is extended or adjusted under 35 U.S.C. 154(b) by 471 days.

(21) Appl. No.: 17/974,902

(22) Filed: Oct. 27, 2022

(65) Prior Publication Data

US 2024/0138905 A1 May 2, 2024

(51) Int. Cl.
A61B 18/14 (2006.01)
A61B 18/00 (2006.01)

(52) U.S. Cl.
CPC .............. *A61B 18/1492* (2013.01); *A61B 2018/00577* (2013.01); *A61B 2018/00839* (2013.01); *A61B 2218/002* (2013.01)

(58) Field of Classification Search
CPC ...... A61B 18/1492; A61B 2018/00577; A61B 2018/00839; A61B 2218/002
See application file for complete search history.

(56) References Cited

U.S. PATENT DOCUMENTS

| | | | |
|---|---|---|---|
| 5,738,096 A | 4/1998 | Ben-Haim | |
| 8,456,182 B2 | 6/2013 | Bar-Tal et al. | |
| 8,956,353 B2 | 2/2015 | Govari et al. | |
| 9,480,416 B2 | 11/2016 | Govari et al. | |
| 9,801,585 B2 | 10/2017 | Shah et al. | |
| 9,907,480 B2 | 3/2018 | Basu et al. | |
| 10,130,422 B2 | 11/2018 | Ditter | |
| 10,660,700 B2 | 5/2020 | Beeckler et al. | |
| 10,702,177 B2 | 7/2020 | Aujla | |
| 10,743,932 B2 | 8/2020 | Gallardo et al. | |
| 11,559,349 B2 | 1/2023 | Bar-Tal et al. | |
| 11,744,480 B2 | 9/2023 | Hoitink et al. | |
| 2006/0111707 A1 * | 5/2006 | O'Sullivan ............ C08G 73/10 | 606/41 |
| 2007/0282259 A1 * | 12/2007 | Morris .............. A61M 25/0075 | 604/118 |
| 2014/0257282 A1 | 9/2014 | Wang et al. | |
| 2017/0348049 A1 * | 12/2017 | Vrba .................. A61B 18/1492 | |

(Continued)

OTHER PUBLICATIONS

European Extended Search Report and Written Opinion dated Mar. 13, 2024, for Application No. 23206071.5, 6 pages.

*Primary Examiner* — Linda C Dvorak
*Assistant Examiner* — Abigail Bock
(74) *Attorney, Agent, or Firm* — FBT Gibbons LLP

(57) ABSTRACT

An apparatus includes a body, a catheter, and an end effector. The catheter extends distally from the body and includes a lumen. The end effector includes at least one electrode. The end effector further includes at least one port in fluid communication with the lumen of the catheter such that the lumen is operable to communicate the fluid from a fluid source to the at least one port. The end effector further includes at least one flexible sleeve positioned over the at least one port, the at least one flexible sleeve being configured to transition between a closed state in which the at least one flexible sleeve prevents the fluid from exiting the at least one port, and an open state in which the at least one flexible sleeve permits the fluid to exit the at least one port.

18 Claims, 12 Drawing Sheets

(56) References Cited

U.S. PATENT DOCUMENTS

| | | | |
|---|---|---|---|
| 2018/0036060 A1* | 2/2018 | Wegrzyn, III | A61B 18/082 |
| 2019/0117297 A1* | 4/2019 | Beeckler | A61B 5/055 |
| 2021/0085386 A1 | 3/2021 | Rao et al. | |
| 2021/0196374 A1* | 7/2021 | Xu | A61B 18/1492 |
| 2022/0257093 A1 | 8/2022 | Tarke et al. | |

* cited by examiner

IRRIGATION TUBING WITH REGULATED FLUID EMISSION

BACKGROUND

Cardiac arrhythmias, such as atrial fibrillation, occur when regions of cardiac tissue abnormally conduct electric signals. Procedures for treating arrhythmia include surgically disrupting the conducting pathway for such signals. By selectively ablating cardiac tissue by application of electrical energy (e.g., radiofrequency (AC type) or irreversible electroporation (IRE), such as pulsed field (DC type) energy), it may be possible to cease or modify the propagation of unwanted electrical signals from one portion of the heart to another. The ablation process may provide a barrier to unwanted electrical pathways by creating electrically insulative lesions or scar tissue that effectively block communication of aberrant electrical signals across the tissue.

In some procedures, a catheter with one or more electrodes may be used to provide ablation within the cardiovascular system. The catheter may be inserted into a major vein or artery (e.g., the femoral artery) and then advanced to position the electrodes within the heart or in a cardiovascular structure adjacent to the heart (e.g., the pulmonary vein). The one or more electrodes may be placed in contact with cardiac tissue or other vascular tissue and then activated with electrical energy to thereby ablate the contacted tissue. In some cases, the electrodes may be bipolar. In some other cases, a monopolar electrode may be used in conjunction with a ground pad or other reference electrode that is in contact with the patient. Irrigation may be used to draw heat from ablating components of an ablation catheter; and to prevent the formation of blood clots near the ablation site.

Examples of ablation catheters are described in U.S. Pub. No. 2013/0030426, entitled "Integrated Ablation System using Catheter with Multiple Irrigation Lumens," published Jan. 31, 2013, the disclosure of which is incorporated by reference herein, in its entirety; U.S. Pub. No. 2017/0312022, entitled "Irrigated Balloon Catheter with Flexible Circuit Electrode Assembly," published Nov. 2, 2017, the disclosure of which is incorporated by reference herein, in its entirety; U.S. Pub. No. 2018/0071017, entitled "Ablation Catheter with a Flexible Printed Circuit Board," published Mar. 15, 2018, the disclosure of which is incorporated by reference herein, in its entirety; U.S. Pub. No. 2018/0056038, entitled "Catheter with Bipole Electrode Spacer and Related Methods," published Mar. 1, 2018, the disclosure of which is incorporated by reference herein, in its entirety; U.S. Pat. No. 10,130,422, entitled "Catheter with Soft Distal Tip for Mapping and Ablating Tubular Region," issued Nov. 20, 2018, the disclosure of which is incorporated by reference herein, in its entirety; U.S. Pat. No. 8,956,353, entitled "Electrode Irrigation Using Micro-Jets," issued Feb. 17, 2015, the disclosure of which is incorporated by reference herein, in its entirety; and U.S. Pat. No. 9,801,585, entitled "Electrocardiogram Noise Reduction," issued Oct. 31, 2017, the disclosure of which is incorporated by reference herein, in its entirety.

Some catheter ablation procedures may be performed after using electrophysiology (EP) mapping to identify tissue regions that should be targeted for ablation. Such EP mapping may include the use of sensing electrodes on a catheter (e.g., the same catheter that is used to perform the ablation or a dedicated mapping catheter). Such sensing electrodes may monitor electrical signals emanating from conductive endocardial tissues to pinpoint the location of aberrant conductive tissue sites that are responsible for the arrhythmia. Examples of an EP mapping system are described in U.S. Pat. No. 5,738,096, entitled "Cardiac Electromechanics," issued Apr. 14, 1998, the disclosure of which is incorporated by reference herein, in its entirety. Examples of EP mapping catheters are described in U.S. Pat. No. 9,907,480, entitled "Catheter Spine Assembly with Closely-Spaced Bipole Microelectrodes," issued Mar. 6, 2018, the disclosure of which is incorporated by reference herein, in its entirety; U.S. Pat. No. 10,130,422, entitled "Catheter with Soft Distal Tip for Mapping and Ablating Tubular Region," issued Nov. 20, 2018, the disclosure of which is incorporated by reference herein, in its entirety; and U.S. Pub. No. 2018/0056038, entitled "Catheter with Bipole Electrode Spacer and Related Methods," published Mar. 1, 2018, the disclosure of which is incorporated by reference herein, in its entirety.

Some catheter procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO 3® system by Biosense Webster, Inc. of Irvine, California. Examples of catheters that are configured for use with an IGS system are disclosed in U.S. Pat. No. 9,480,416, entitled "Signal Transmission Using Catheter Braid Wires," issued Nov. 1, 2016, the disclosure of which is incorporated by reference herein, in its entirety; and various other references that are cited herein.

While several catheter systems and methods have been made and used, it is believed that no one prior to the inventors has made or used the invention described, illustrated and claimed herein.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION FOR MODES OF CARRYING OUT THE INVENTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 70% to 110%. In addition, as used herein, the terms "patient," "host," "user," and "subject" refer to any human or animal subject and are not intended to limit the systems or methods to human use, although use of the subject invention in a human patient represents a preferred embodiment.

I. Overview of Example of a Catheter System

Figure 1:
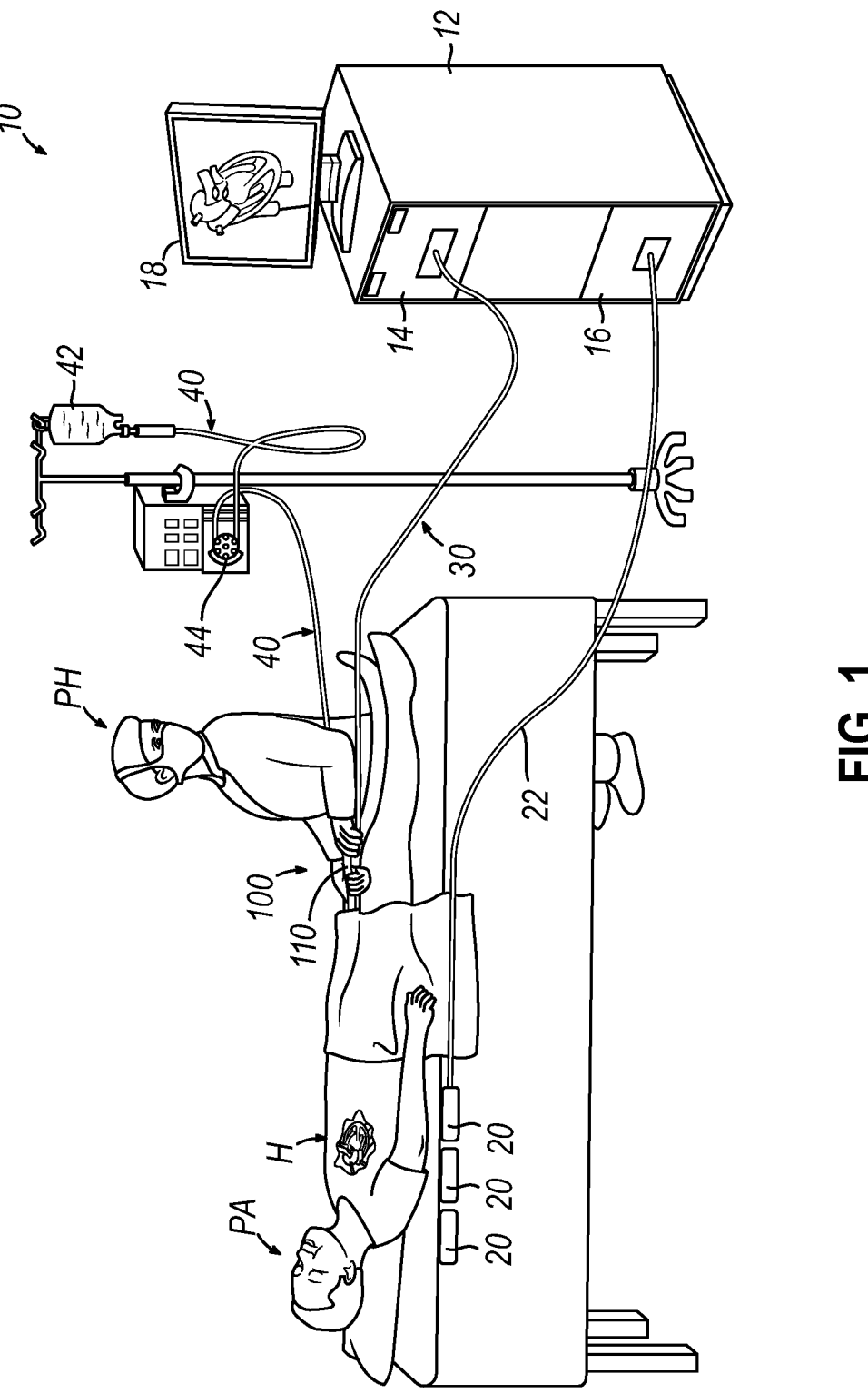
FIG. 1 depicts a schematic view of a medical procedure in which a catheter of a catheter assembly is inserted in a patient.
Figure 2A:
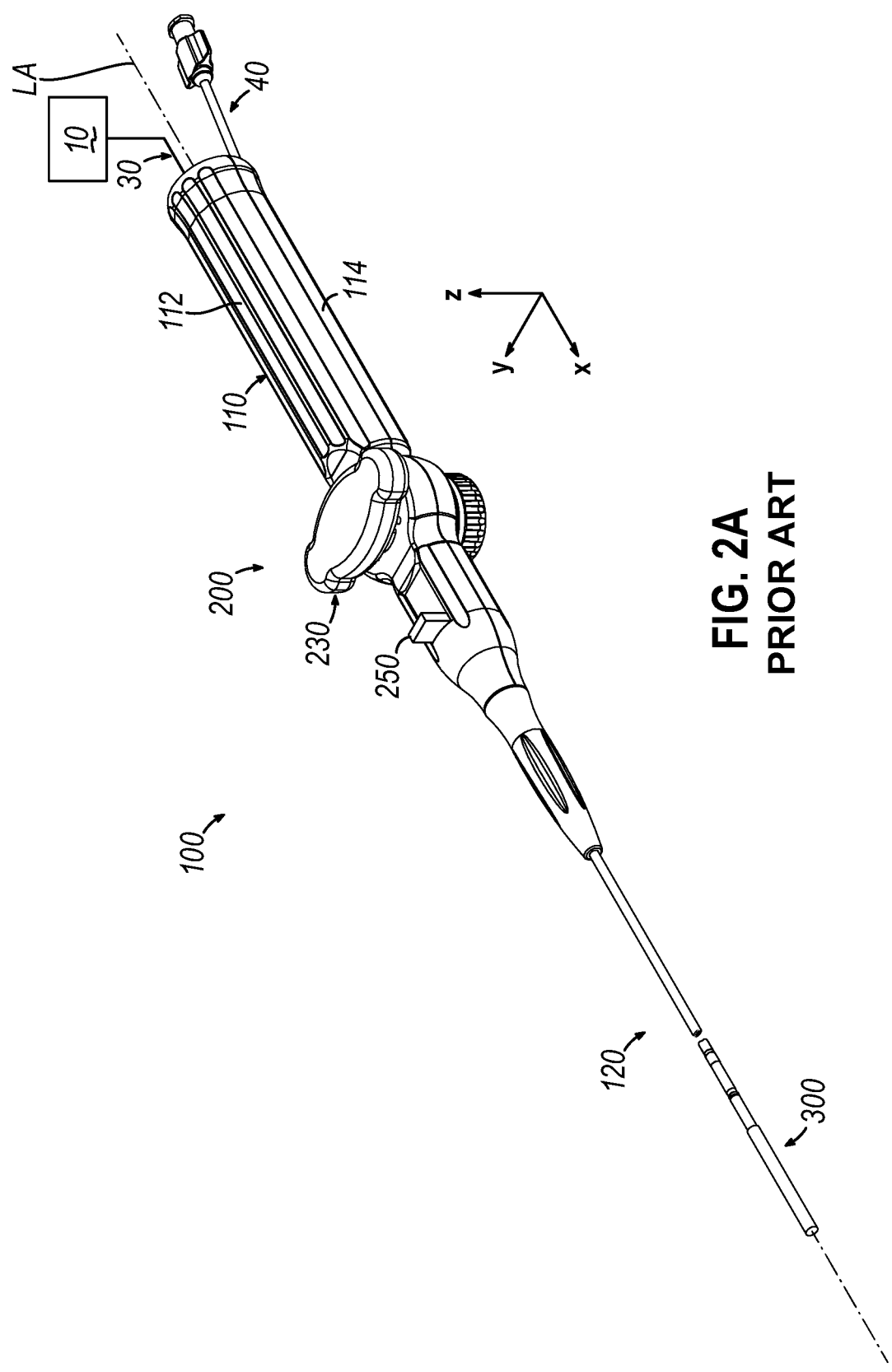
FIG. 2A depicts a perspective view of the catheter assembly of FIG. 1, with additional components shown in schematic form, with an end effector in a non-expanded state, and with the end effector being shown schematically.
Figure 2B:
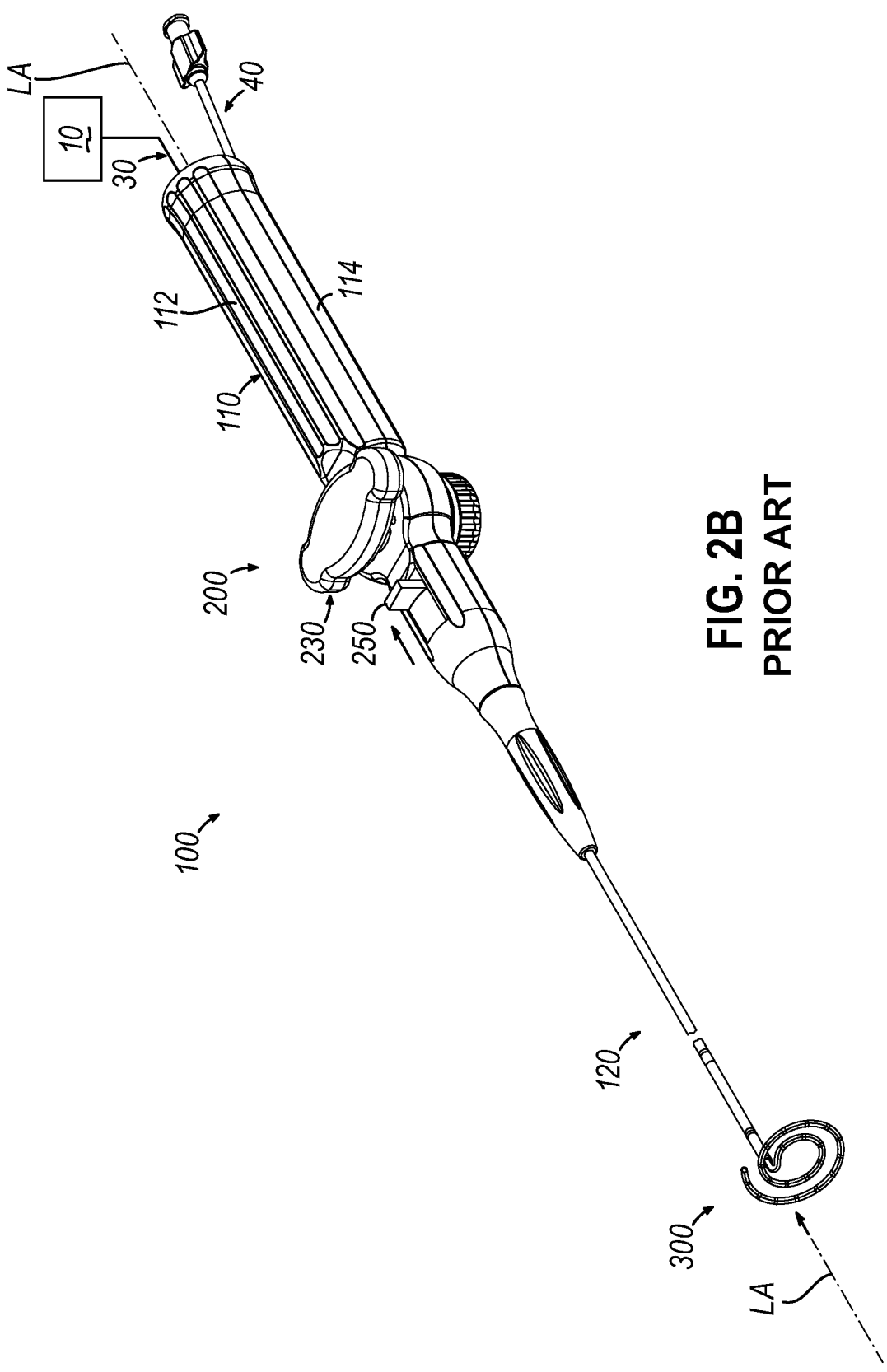
FIG. 2B depicts a perspective view of the catheter assembly of FIG. 1, with additional components shown in schematic form, and with the end effector in an expanded state.

FIG. 1 shows an exemplary medical procedure and associated components of a cardiac catheter system that may be used to provide EP mapping and/or cardiac ablation as referred to above. In particular, FIG. 1 shows a physician (PH) grasping a handle assembly (110) of a catheter assembly (100), with an end effector (300) of a catheter (120) (shown in FIGS. 2A-3 but not shown in FIG. 1) of catheter assembly (100) disposed in a patient (PA) to map potentials in tissue and/or ablate tissue in or near the heart (H) of the patient (PA). As shown in FIGS. 2A-2B, catheter assembly (100) includes handle assembly (110), catheter (120) extending distally from handle assembly (110), end effector (300) located at a distal end of catheter (120), and a deflection drive assembly (200) associated with handle assembly (110).

As will be described in greater detail below, end effector (300) may include various electrodes, sensors, and/or other features that are configured to deliver electrical energy (e.g., RF or IRE, etc.) to targeted tissue sites, provide EP mapping functionality, track external forces imparted on end effector (300), track the location of end effector (300), and/or disperse fluid. As will also be described in greater detail below, deflection drive assembly (200) is configured to deflect end effector (300) and a distal portion of catheter (120) away from a central longitudinal axis (LA) defined by a proximal portion of catheter (120).

Figure 3:
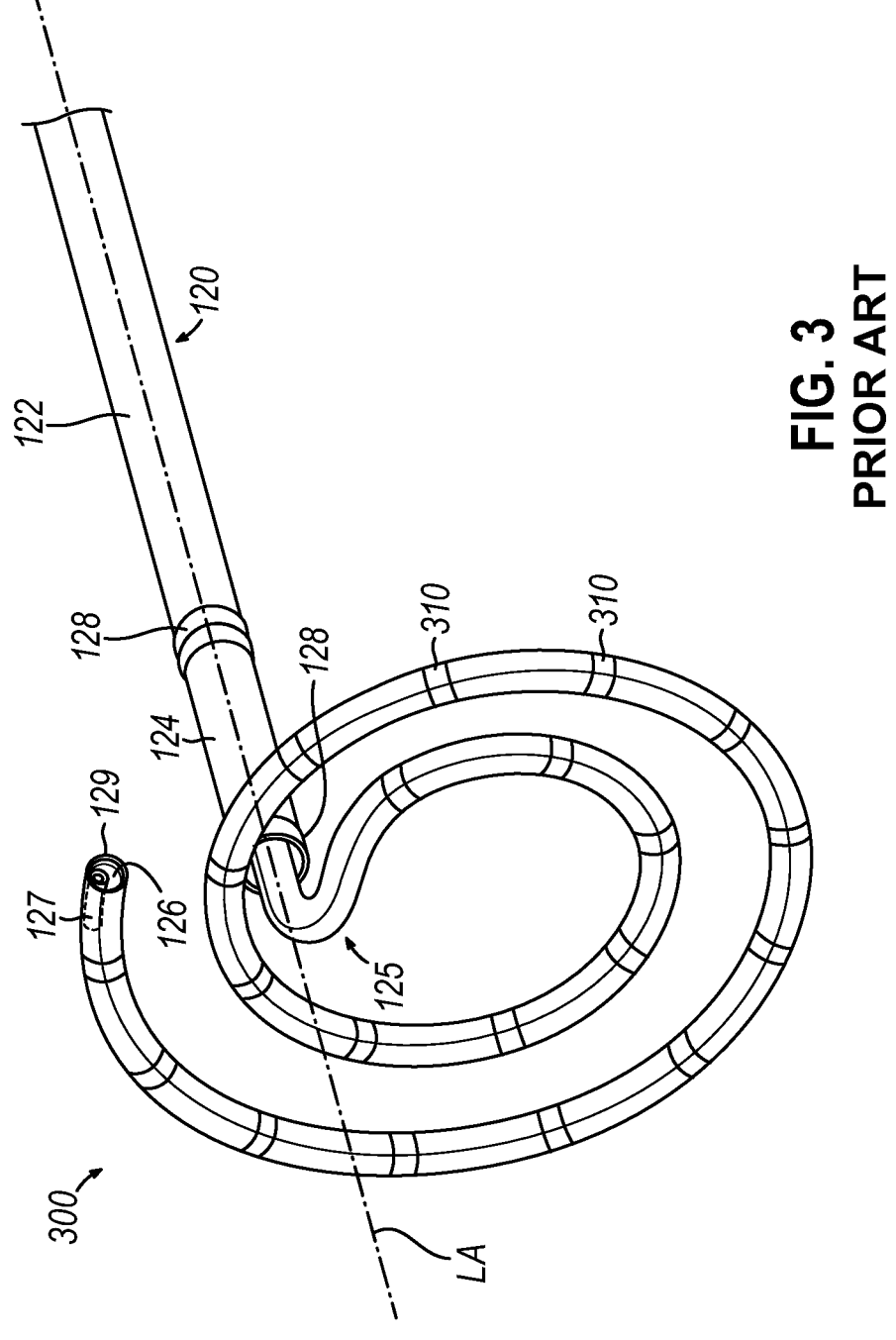
FIG. 3 depicts a perspective view of the end effector of FIG. 2A in the expanded state.

As shown in FIG. 3, catheter (120) includes an elongate flexible sheath (122), with end effector (300) being disposed at a distal end (125) of a first inner shaft (124) extending distally from sheath (122). End effector (300) and various components that are contained in sheath (122) will be described in greater detail below. Catheter assembly (100) is coupled with a guidance and drive system (10) via a cable (30). Catheter assembly (100) is also coupled with a fluid source (42) via a fluid conduit (40). A set of magnetic field generators (20) are positioned underneath the patient (PA) and are coupled with guidance and drive system (10) via another cable (22). Magnetic field generators (20) are merely optional.

As shown in FIG. 1, guidance and drive system (10) of the present example include a console (12) and a display (18). Console (12) includes a first driver module (14) and a second driver module (16). First driver module (14) is coupled with catheter assembly (100) via cable (30). In some variations, first driver module (14) is operable to receive EP mapping signals obtained via electrodes (310) of end effector (300) as described in greater detail below. Console (12) includes a processor (not shown) that processes such EP mapping signals and thereby provides EP mapping as is known in the art.

In versions where electrodes (310) are operable to provide ablation, first driver module (14) may be operable to provide electrical energy (e.g., RF or IRE) to such ablation electrodes (310), to thereby ablate tissue contacting the ablation electrodes. Second driver module (16) is coupled with magnetic field generators (20) via cable (22). Second driver module (16) is operable to activate magnetic field generators (20) to generate an alternating magnetic field around the heart (H) of the patient (PA). For instance, magnetic field generators (20) may include coils that generate alternating magnetic fields in a predetermined working volume that contains the heart (H).

First driver module (14) is also operable to receive position indicative signals from a position sensor (127) in end effector (300). In such versions, the processor of console (12) is also operable to process the position indicative signals from position sensor (127) to thereby determine the position of end effector (300) within the patient (PA). In some versions, position sensor (127) includes two or more coils on respective panels that are operable to generate signals that are indicative of the position and orientation of end effector (300) within the patient (PA). The coils are configured to generate electrical signals in response to the presence of an alternating electromagnetic field generated by magnetic field generators (20). Other components and techniques that may be used to generate real-time position data associated with end effector (300) may include wireless triangulation, acoustic tracking, optical tracking, inertial tracking, and the like. Alternatively, end effector (300) may lack a position sensor (127).

Display (18) is coupled with the processor of console (12) and is operable to render images of patient anatomy. Such images may be based on a set of preoperatively or intraoperatively obtained images (e.g., a CT or MM scan, 3-D map, etc.). The views of patient anatomy provided through display (18) may also change dynamically based on signals from position sensor (127) of end effector (300). For instance, as end effector (300) of catheter (120) moves within the patient (PA), the corresponding position data from position sensor (127) may cause the processor of console (12) to update the patient anatomy views in display (18) in real time to depict the regions of patient anatomy around end effector (300) as end effector (300) moves within the patient (PA). Moreover, the processor of console (12) may drive display (18) to show locations of aberrant conductive tissue sites, as detected via electrophysiological (EP) mapping with end effector (300) or as otherwise detected (e.g., using a dedicated EP mapping catheter, etc.). By way of example only, the processor of console (12) may drive display (18) to superimpose the locations of aberrant conductive tissue sites on the images of the patient's anatomy, such as by superimposing an illuminated dot, a crosshair, or some other form of visual indication of aberrant conductive tissue sites.

The processor of console (12) may also drive display (18) to superimpose the current location of end effector (300) on the images of the patient's anatomy, such as by superimposing an illuminated dot, a crosshair, a graphical representation of end effector (300), or some other form of visual indication. Such a superimposed visual indication may also move within the images of the patient anatomy on display (18) in real time as the physician moves end effector (300) within the patient (PA), thereby providing real-time visual feedback to the operator about the position of end effector (300) within the patient (PA) as end effector (300) moves within the patient (PA). The images provided through display (18) may thus effectively provide a video tracking the position of end effector (300) within a patient (PA), without necessarily having any optical instrumentation (i.e., cameras) viewing end effector (300). In the same view, display (18) may simultaneously visually indicate the locations of aberrant conductive tissue sites detected through EP mapping. The physician (PH) may thus view display (18) to observe the real time positioning of end effector (300) in relation to the mapped aberrant conductive tissue sites and in relation to images of the adjacent anatomical structures in the patient (PA).

Fluid source (42) of the present example includes a bag containing saline or some other suitable irrigation fluid. Conduit (40) includes a flexible tube that is further coupled with a pump (44), which is operable to selectively drive fluid from fluid source (42) to catheter assembly (100). As described in greater detail below, such irrigation fluid may be expelled through the open distal end (129) of a second inner shaft (126) of end effector (300) and/or through irrigation ports (150) of second inner shaft (126). Such irrigation may be provided in any suitable fashion as will be apparent to those skilled in the art in view of the teachings herein.

As shown in FIGS. 2A-2B, end effector (300) of the present example is operable to transition between a non-expanded state (FIG. 2A) and an expanded state (FIG. 2B). As will be described in greater detail below, this transitioning is driven by manipulation of an end effector expansion actuator (250) of handle assembly (110). In some versions, outer sheath (122) is configured to selectively slide over end effector (300) when end effector (300) is in the non-expanded state. In such versions, outer sheath (122) may be retracted proximally to expose end effector (300) to thereby enable end effector (300) to transition to the expanded state.

In the version depicted in in FIG. 3, end effector (300) is configured to define a spiral shape when in the expanded shape. End effector (300) of the example shown in FIG. 3 is mounted to first inner shaft (124), which is internal to outer sheath (122). End effector (300) of this example includes a plurality of electrodes (310) spaced apart from each other along a second inner shaft (126), which protrudes from open distal end (125) of first inner shaft (124). In some versions, electrodes (310) are operable to provide bipolar EP mapping by picking up electrocardiogram signals from tissue as is known in the art. Electrodes (310) may cooperate in pairs in some implementations. Signals picked up by electrodes (310) may be communicated back through electrical conduits (not shown) in catheter (120) to console (12), which may process the signals to provide EP mapping to thereby identify locations of aberrant electrical activity within the cardiac anatomy. This may in turn allow the physician (PH) to identify the most appropriate regions of cardiac tissue to ablate (e.g., with RF energy, IRE energy, cryoablation, etc.), to thereby prevent or at least reduce the communication of aberrant electrical activity across the cardiac tissue.

As also shown in FIG. 3, a pair of reference electrodes (128) are coaxially positioned about shaft (124). Such reference electrodes (128) may be utilized in conjunction with electrode pairs (330) during an EP mapping procedure. For instance, reference electrodes (128) may be utilized to pick up reference potentials from blood or saline that passes through the interior of end effector (300) during an EP mapping procedure. Such reference potentials may be used to reduce noise or far field signals, as is known in the art. In the present example, end effector (300) is configured such that reference electrodes (128) are positioned to avoid contacting tissue during use of end effector (300) in an EP mapping procedure; while still allowing blood and saline to flow freely through end effector (300) to reach reference electrodes (128).

By way of example only, electrodes (128, 310) may be formed of platinum, gold, or any other suitable material. Electrodes (128, 310) may include various coatings, if desired. For instance, electrode pairs (330) may include a coating that is selected to improve the signal-to-noise ratio of signals from electrode pairs (330). Such coatings may include, but need not be limited to, iridium oxide (IrOx) coating, poly(3,4-ethylenedioxythiophene) (PEDOT) coating, Electrodeposited Iridium Oxide (EIROF) coating, Platinum Iridium (PtIr) coating, or any other suitable coating. Various suitable kinds of coatings that may be used for electrodes (128, 310) will be apparent to those skilled in the art in view of the teachings herein.

While only EP mapping electrodes (310) are shown in FIG. 3, other versions of end effector (300) may include ablation electrodes in addition to, or in lieu of, including EP mapping electrodes (310). Such ablation electrodes may be used to apply electrical energy to tissue that is in contact with the ablation electrodes, to thereby ablate the tissue. Each ablation electrode may be coupled with a corresponding trace or other electrical conduit on end effector (300), thereby enabling console (12) to communicate electrical energy through electrical conduits (not shown) in catheter (120) to the traces or other conduits on end effector (300) to reach the ablation electrodes. Such electrical energy may include radiofrequency (AC type) electrical energy, pulsed field (DC type) electrical energy (e.g., irreversible electroporation, etc.), or some other form of electrical energy. In some versions where end effector (300) is operable to apply ablation, such ablation may be provided via electrodes (310).

End effector (300) of the present example further includes a position sensor (127) located near distal end (129) of second inner shaft (126). Position sensor (127) is operable to generate signals that are indicative of the position and orientation of end effector (300) within the patient (PA). By way of example only, position sensor (127) may be in the form of a wire coil or a plurality of wire coils (e.g., three orthogonal coils) that are configured to generate electrical signals in response to the presence of an alternating electromagnetic field generated by magnetic field generators (20). Position sensor (127) may be coupled with wire, a trace, or any other suitable electrical conduit along or otherwise through catheter (120), thereby enabling signals generated by position sensor (127) to be communicated back through electrical conduits (not shown) in catheter (120) to console (12). Console (12) may process the signals from position sensor (127) to identify the position of end effector (300) within the patient (PA). Other components and techniques that may be used to generate real-time position data associated with end effector (300) may include wireless triangulation, acoustic tracking, optical tracking, inertial tracking, and the like. In some versions, position sensor (127) may be omitted.

As noted above, catheter assembly (100) of the present example is coupled with a fluid source (42) via a fluid conduit (40). A fluid conduit (not shown) extends along the length of catheter (120) and is operable to deliver irrigation fluid (e.g., saline) out through the open distal end (129) of second inner shaft (126). For instance, the fluid conduit may distally terminate at distal end (129). In addition, or in the alternative, second inner shaft (126) may incorporate one or more laterally oriented irrigation ports (150) (FIG. 6) that are extend radially through a sidewall of second inner shaft (126) and are in fluid communication with fluid conduit (40) via the fluid conduit extending along the length of catheter (120). Ports (150) thus allow irrigation fluid to be communicated from fluid source (42) out through second inner shaft (126). Such irrigation ports (150) may be spaced apart along the region of length of inner shaft (126) corresponding to the longitudinal position of end effector (300).

Figure 6:
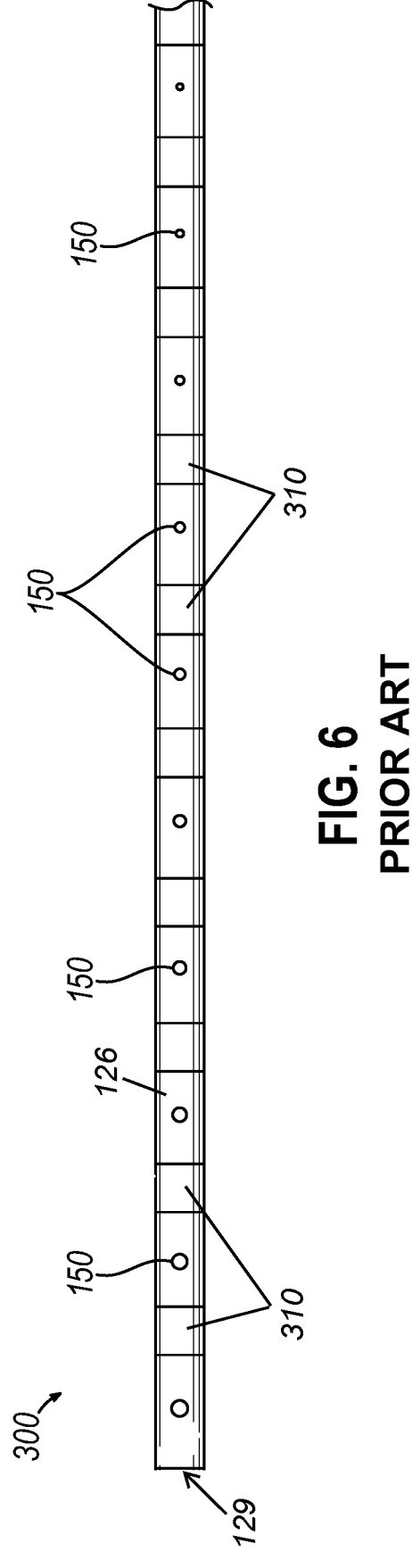
FIG. 6 depicts a side elevational view of a portion of the end effector of FIG. 2A in the non-expanded state.

In the example shown in FIG. 6, ports (150) have different aperture sizes, based on the position of each port (150) along the length of inner shaft (126). In particular, the aperture size of ports (150) progressively increases along the length of second inner shaft (126) in the distal direction. Such a configuration may ensure that a sufficient volume of irrigation fluid reaches the relatively distal ports (150) rather than escaping out through the relatively proximal ports (150), to thereby promote suitable delivery of irrigation fluid out through all ports (150). The progressively increasing aperture size of ports (150) thus provides a fluid basing effect along the length of second inner shaft (126). This biasing of ports (150) may be tailored to a particular inlet volumetric flow rate of the irrigation fluid in order to achieve a desired downstream flow distribution of the irrigation fluid.

In versions that include irrigation ports (150), distal end (129) of a second inner shaft (126) may be closed instead of being open. In either case, the irrigation fluid expelled via irrigation ports (150) and/or an open version of distal end (129) may provide cooling, flushing, or other effects at end effector (300) during operation of end effector (300) within the patient (PA). Various suitable ways in which catheter assembly (100) may provide irrigation will be apparent to those skilled in the art in view of the teachings herein. Alternatively, some variations of catheter assembly (100) may lack irrigation capabilities, such that conduit (40), fluid source (42), and pump (44) may be omitted.

In addition to the foregoing, end effector (300) and other aspects of catheter assembly (100) may be configured and operable in accordance with at least some of the teachings of any one or more of the various patent documents that are incorporated by reference herein.

As noted above, catheter assembly (100) includes a deflection drive assembly (200) that is configured to deflect end effector (300) away from the central longitudinal axis (LA) defined by a proximal portion of catheter (120). Deflection drive assembly (200) of the present example incudes drive cables (160, 170), a cable driver assembly (210), and a rocker arm (230). As will be described in greater detail below, the physician (PH) may actuate rocker arm (230) relative to handle assembly (110) such that cable driver assembly (210) actuates drive cables (160, 170) in a simultaneous, longitudinally-opposing motion to selectively deflect end effector (300) laterally away from a longitudinal axis (LA), thereby enabling the physician (PH) to actively steer end effector (300) within the patient (PA).

Figures 4A, 5A:
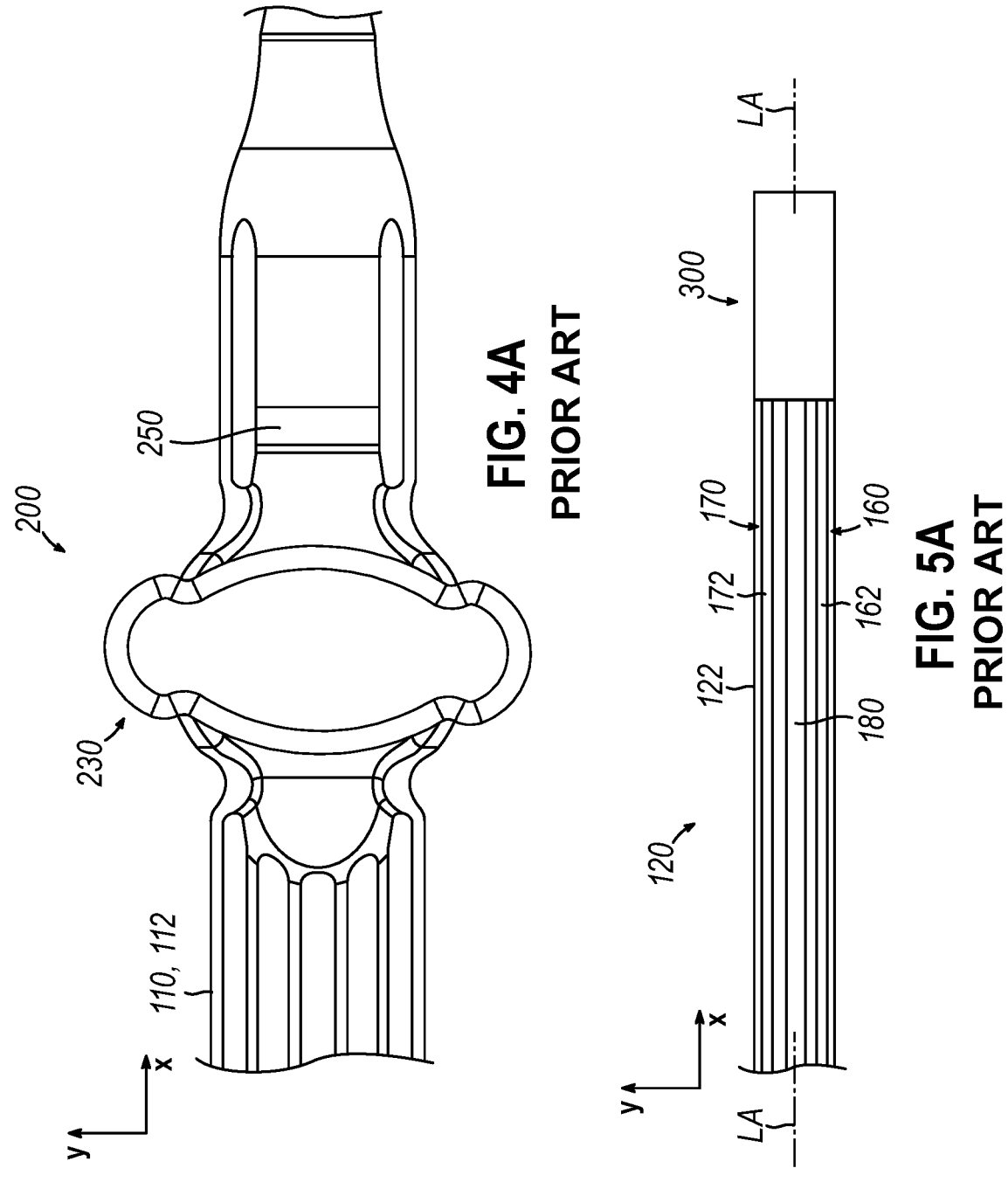
FIG. 4A depicts a top plan view of a portion of a handle assembly of the catheter assembly of FIG. 1, with an articulation drive actuator in a first rotational position.
FIG. 5A depicts a top plan view of the distal portion of the catheter of the catheter assembly of FIG. 1, with a portion of the catheter in cross-section, with the end effector being shown schematically, and with the distal portion in a non-deflected state associated with the first rotational position of the articulation drive actuator of FIG. 4A.
Figures 4B, 5B:
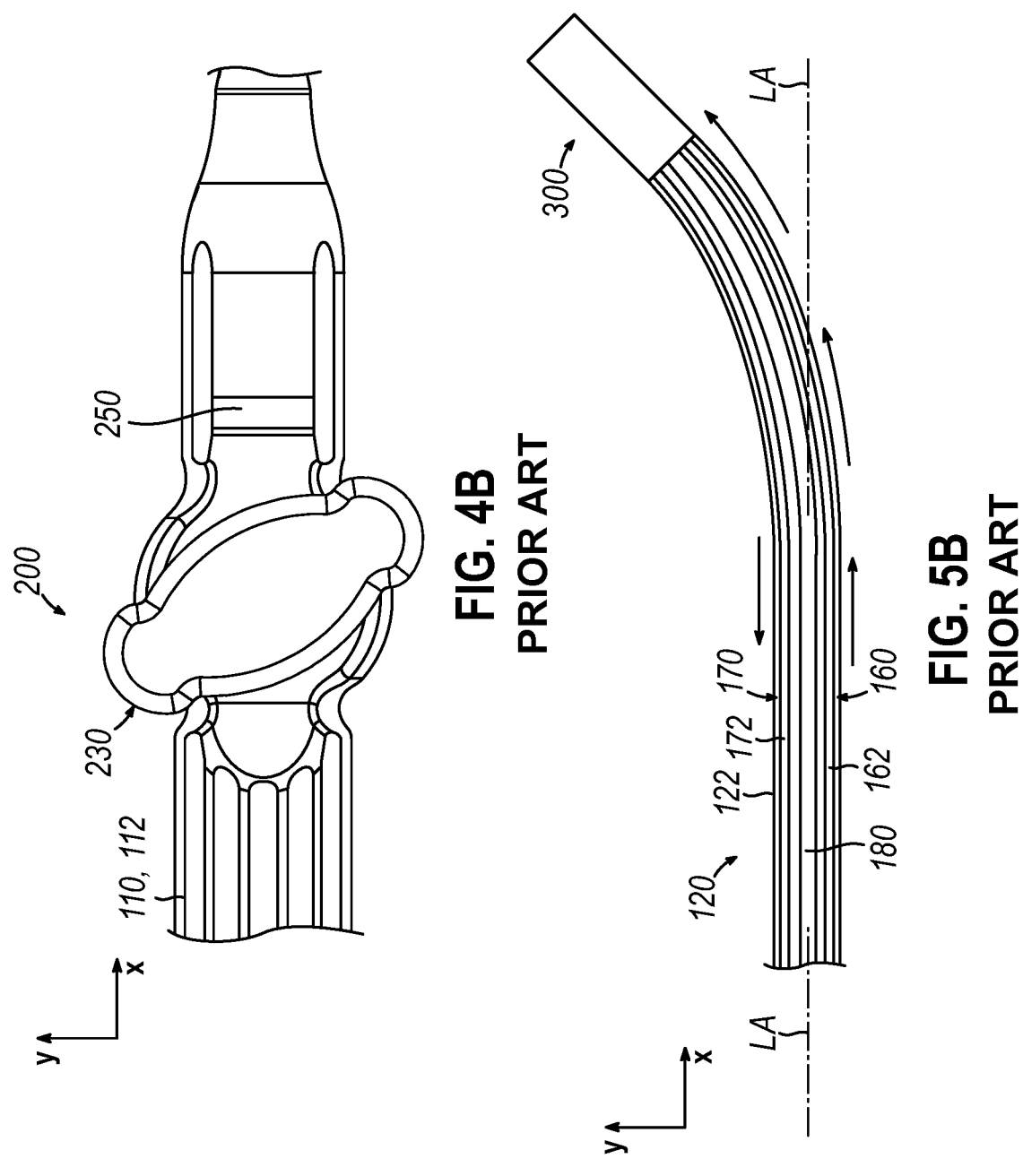
FIG. 4B depicts a top plan view of a portion of the handle assembly of FIG. 4A, with the articulation drive actuator in a second rotational position
FIG. 5B depicts a top plan view of the distal portion of the catheter of FIG. 5A, with a portion of the catheter in cross-section, with the end effector being shown schematically, and with the distal portion in a first deflected state associated with the second rotational position of the articulation drive actuator of FIG. 4B.
Figures 4C, 5C:
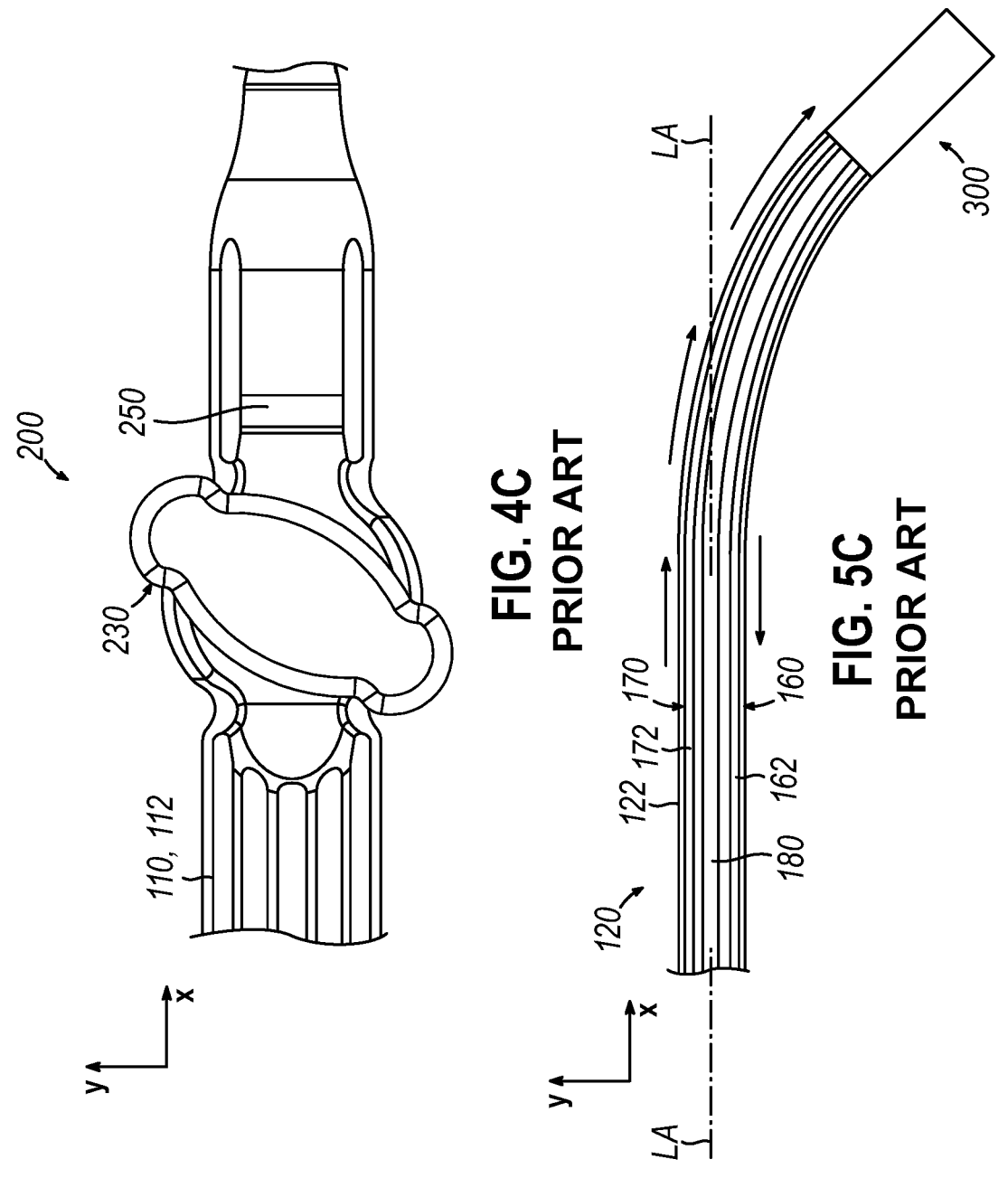
FIG. 4C depicts a top plan view of a portion of the handle assembly of FIG. 4A, with the articulation drive actuator in a third rotational position.
FIG. 5C depicts a top plan view of the distal portion of the catheter of FIG. 5A, with a portion of the catheter in cross-section, with the end effector being shown schematically, and with the distal portion in a second deflected state associated with the third rotational position of the articulation drive actuator of FIG. 4C.

Selected portions of deflection drive assembly (200) are operatively coupled to handle (110). Handle (110) includes a first casing portion (112) and a second casing portion (114) together defining an internal cavity (not shown). Drive cables (160, 170) include respective intermediary portions (162, 172), distal portions (not shown), and proximal end blocks (not shown). The proximal end blocks serve as a mechanical ground for drive cables (160, 170). The distal end portions are coupled with end effector (140) to prevent drive cables (160, 170) from being pulled proximally out of end effector (140). Suitable ways in which drive cables (160, 170) may be coupled with end effector (140) will be apparent to those skilled in the art in view of the teachings herein. Intermediary portions (162, 172) extend proximally from the distal portions, through elongate flexible sheath (122) of catheter (120) (as best shown in FIGS. 5A-5C), into the cable driver assembly, and terminate into proximal end blocks. Intermediary portions (162, 172) each wrap around a portion of the cable driver assembly such that movement of the cable driver assembly relative to handle (110) may actuate drive cables (160, 170) simultaneously in opposite directions. The cable driver assembly is rotationally coupled with handle (110). Specifically, cable driver (210) is configured to rotate about a drive axis such that suitable rotation of rocker arm (230) relative to handle (110) may drive rotation of cable driver (210) about a drive axis (D-A).

FIGS. 4A-5C show exemplary use of deflection drive assembly (200) to deflect end effector (140) and the distal portion of catheter (120) about central longitudinal axis (L-L). FIGS. 4A and 5A show various sections of catheter assembly (100) when end effector (140) is in a neutral, non-deflected position. FIG. 4A shows rocker arm (230) in a neutral rotational position relative to handle (110). When rocker arm (230) is in the first rotational position, the cable driver assembly is in a corresponding first rotation position such that drive cables (160, 170) are in a first longitudinal position associated with end effector (140) being in the non-deflected position as shown in FIG. 5A.

When the physician (PH) desires to deflect end effector (140) in a first direction relative to central longitudinal axis (L-L) to a first deflected position shown in FIG. 5B, the physician (PH) may rotate rocker arm (230) relative to handle (110) to the position shown in FIG. 4B. Rotation of rocker arm (230) to the rotational position shown in FIG. 4B drives the cable driver assembly into a corresponding rotational position such that drive cable (170) is driven proximally and drive cable (160) actuates distally, to thereby drive end effector (140) to bend to the position shown in FIG. 5B.

Similarly, when the physician (PH) desires to deflect end effector (140) in a second direction relative to central longitudinal axis (L-L) to a second deflected position shown in FIG. 5C, the physician (PH) may rotate rocker arm (230) relative to handle (110) to the position shown in FIG. 4C. Rotation of rocker arm (230) to the rotational position shown in FIG. 4C drives the cable driver assembly into a corresponding rotational position such that drive cable (160) is driven proximally and drive cable (170) actuates distally, to thereby drive end effector (140) to bend to the position shown in FIG. 5C.

Various other suitable mechanisms that may be used to actuate drive cables (160, 170) in a simultaneous, longitudinally-opposing fashion will be apparent to those skilled in the art in view of the teachings herein. In some versions, catheter assembly (100) may be configured and operable in accordance with one or more teachings of U.S. Pub. No. 2020/0405182, entitled "Catheter Deflection System with Deflection Load Limiter," published Dec. 31, 2020, the disclosure of which is incorporated by reference herein; and/or U.S. Pub. No. 2021/0085386, entitled "Catheter Instrument with Three Pull Wires," published Mar. 25, 2021, the disclosure of which is incorporated by reference herein.

As shown in FIGS. 2A-2B, end effector expansion actuator (250) is operable to drive end effector (300) to transition between a non-expanded state (FIG. 2A) and an expanded state (FIG. 2B). End effector expansion actuator (250) of the present example is in the form of a slider that is operable to translate longitudinally relative to casing portions (112, 114) between a distal position (FIG. 2A) and a proximal position (FIG. 2B). End effector expansion actuator (250) is coupled with end effector (300) via a drive cable (not shown), which extends along the length of catheter (120). A proximal end of drive cable (252) is coupled with a base (not shown) of end effector expansion actuator (250). A distal end of the drive cable is coupled with a corresponding component of end effector (300). Various suitable ways in which the drive cable may be coupled with end effector expansion actuator (250) and second inner shaft (126) will be apparent to those skilled in the art in view of the teachings herein.

In some variations, at least a portion of end effector (300) is resiliently biased to urge end effector (300) toward the expanded state shown in FIGS. 2B and 3. In some such versions, the resilience of end effector (300) may assist the drive cable and second inner shaft (126) in driving end effector (300) toward the expanded state. In some other versions, the drive cable drives the entire length of end effector (300) distally or proximally relative to outer sheath (122). In such versions, outer sheath (122) may compress end effector (300) to reach a non-expanded state when end effector (300) is proximally positioned within outer sheath (122); while the resilience of end effector (300) drives end effector (300) to the expanded state when end effector (300) is positioned distally from outer sheath (122). Other suitable ways in which end effector (300) may transition between the expanded state and the non-expanded state will be apparent to those skilled in the art in view of the teachings herein. Similarly, other suitable ways in which the drive cable may be utilized will be apparent to those skilled in the art in view of the teachings herein. The drive cable may be configured and operable in accordance with one or more teachings of U.S. Pub. No. 2021/0085386, entitled "Catheter Instrument with Three Pull Wires," published Mar. 25, 2021, the disclosure of which is incorporated by reference herein.

II. Example of End Effector with Regulated Irrigation Fluid Delivery

In some procedures, it may be desirable to provide consistent irrigation fluid delivery irrespective of the ambient environment in which end effector (300) is situated. For example, it may be desirable to provide delivery of irrigation fluid with a volumetric flow distribution that is insensitive to whether end effector (300) is situated in open air or immersed in liquid (e.g., saline, blood, etc.), such as to promote reliable and consistent irrigation fluid delivery during performance of an ablation procedure. To that end, it may be desirable to provide features on a catheter that provide a constant back pressure that resists (yet allows) the flow of fluid through one or more openings.

Figures 8A, 8B:
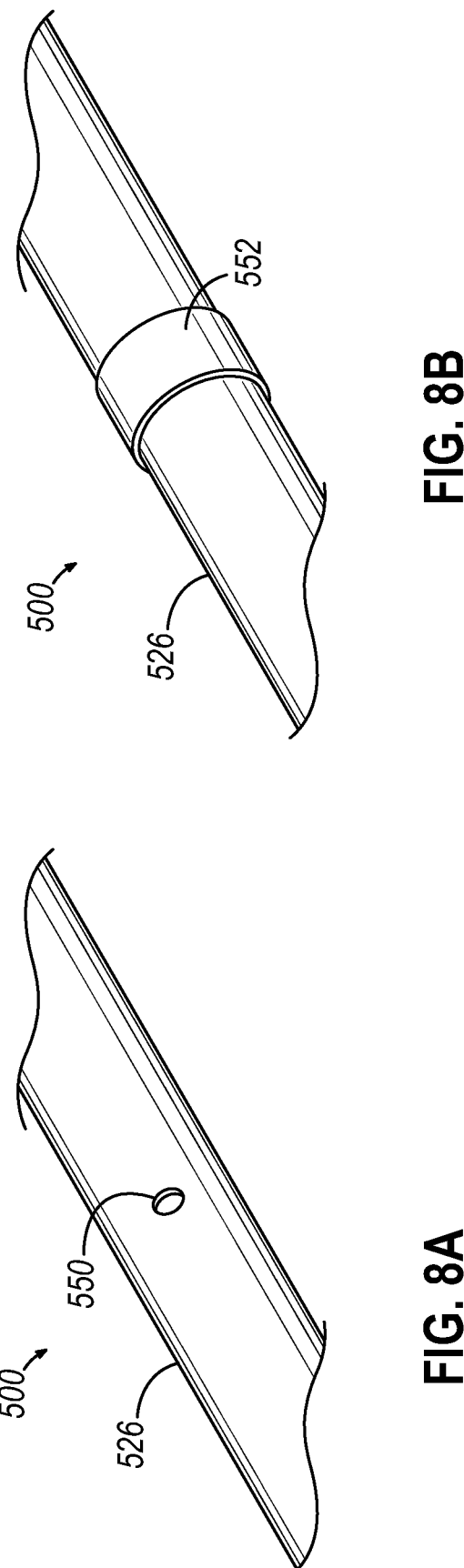
FIG. 8A depicts a perspective view of a portion of the end effector of FIG. 7, with one of the elastic sleeves omitted to show the corresponding irrigation port.
FIG. 8B depicts a perspective view of the portion of FIG. 8A, with the irrigation port covered by the corresponding elastic sleeve.
Figures 8C, 8D:
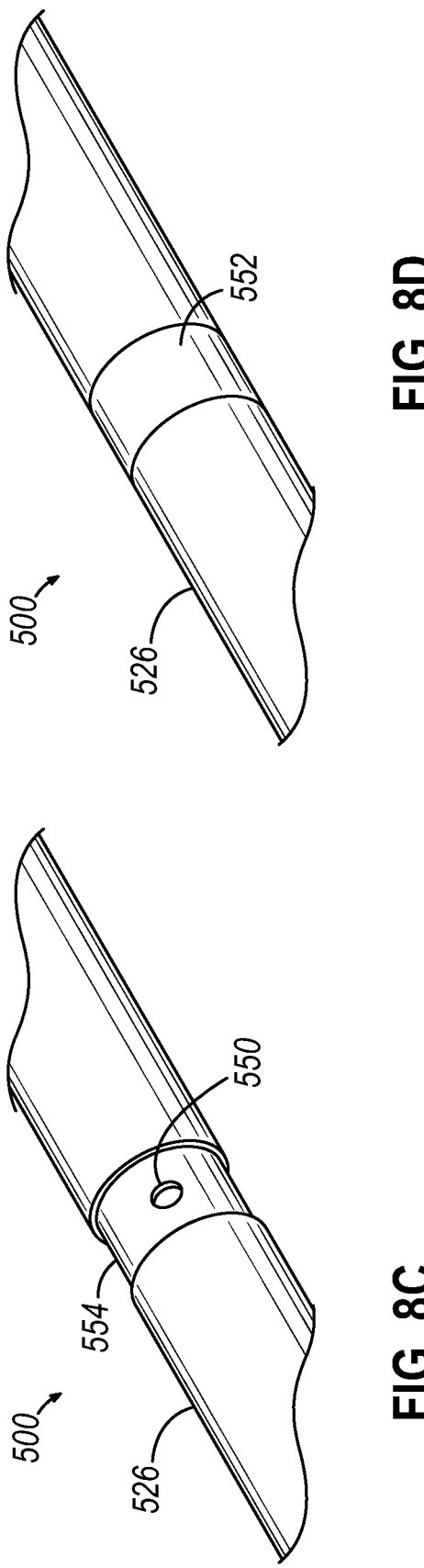
FIG. 8C depicts a perspective view of a portion of the end effector of FIG. 7, with one of the elastic sleeves omitted to show the corresponding irrigation port.
FIG. 8D depicts a perspective view of the portion of FIG. 8C, with the irrigation port covered by the corresponding elastic sleeve.
Figure 9A:
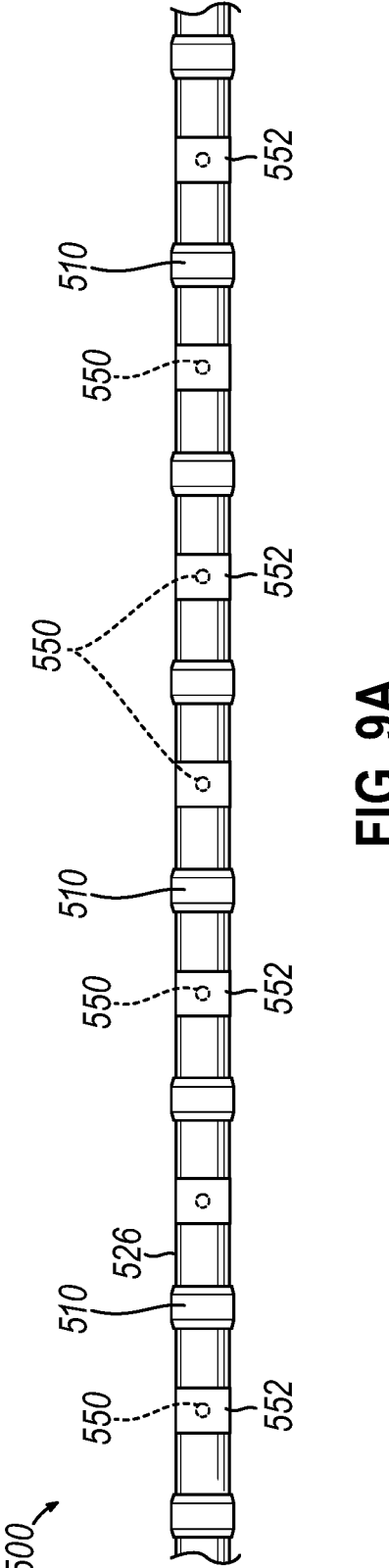
FIG. 9A depicts a side elevational view of the end effector of FIG. 7 in the non-expanded state, with the elastic sleeves in respective closed states.
Figure 9B:
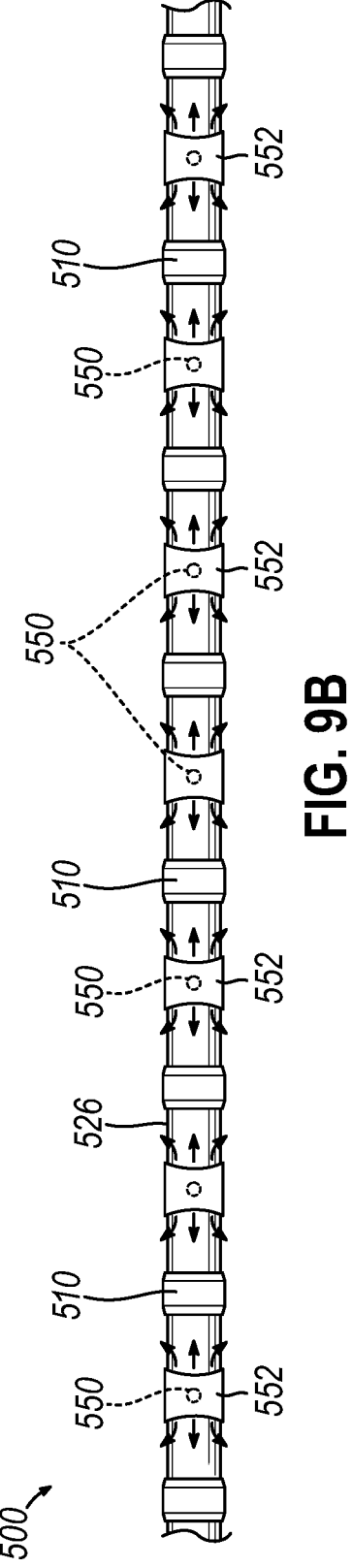
FIG. 9B depicts a side elevational view of the end effector of FIG. 7 in the non-expanded state, with the elastic sleeves in respective open states.

FIGS. 7-9B show an example of a catheter assembly (400) that may function in such a manner and that may be incorporated into the cardiac ablation catheter system of FIG. 1 in place of catheter assembly (100). Catheter assembly (400) may be configured and operable like catheter assembly (100) described above except as otherwise described below. In this regard, catheter assembly (400) includes a handle assembly (not shown) similar to handle assembly (110), a catheter (420) extending distally from the handle assembly, an end effector (500) located at a distal end of catheter (420), and a deflection drive assembly (not shown) similar to deflection drive assembly (200) associated with the handle assembly. The handle assembly may include an end effector expansion actuator (not shown) similar to end effector expansion actuator (250) for transitioning end effector (500) between an expanded state (FIG. 7) and a non-expanded state (FIGS. 9A-9B).

As will be described in greater detail below, end effector (500) includes various electrodes, sensors, and/or other features that are configured to deliver electrical energy (e.g., RF or IRE, etc.) to targeted tissue sites, provide EP mapping functionality, track external forces imparted on end effector (500), track the location of end effector (500), and/or disperse fluid. For example, end effector (500) may be configured and operable in accordance with one or more teachings of U.S. Pub. No. 2021/0085386, entitled "Catheter Instrument with Three Pull Wires," published Mar. 25, 2021, the disclosure of which is incorporated by reference herein.

Figure 7:
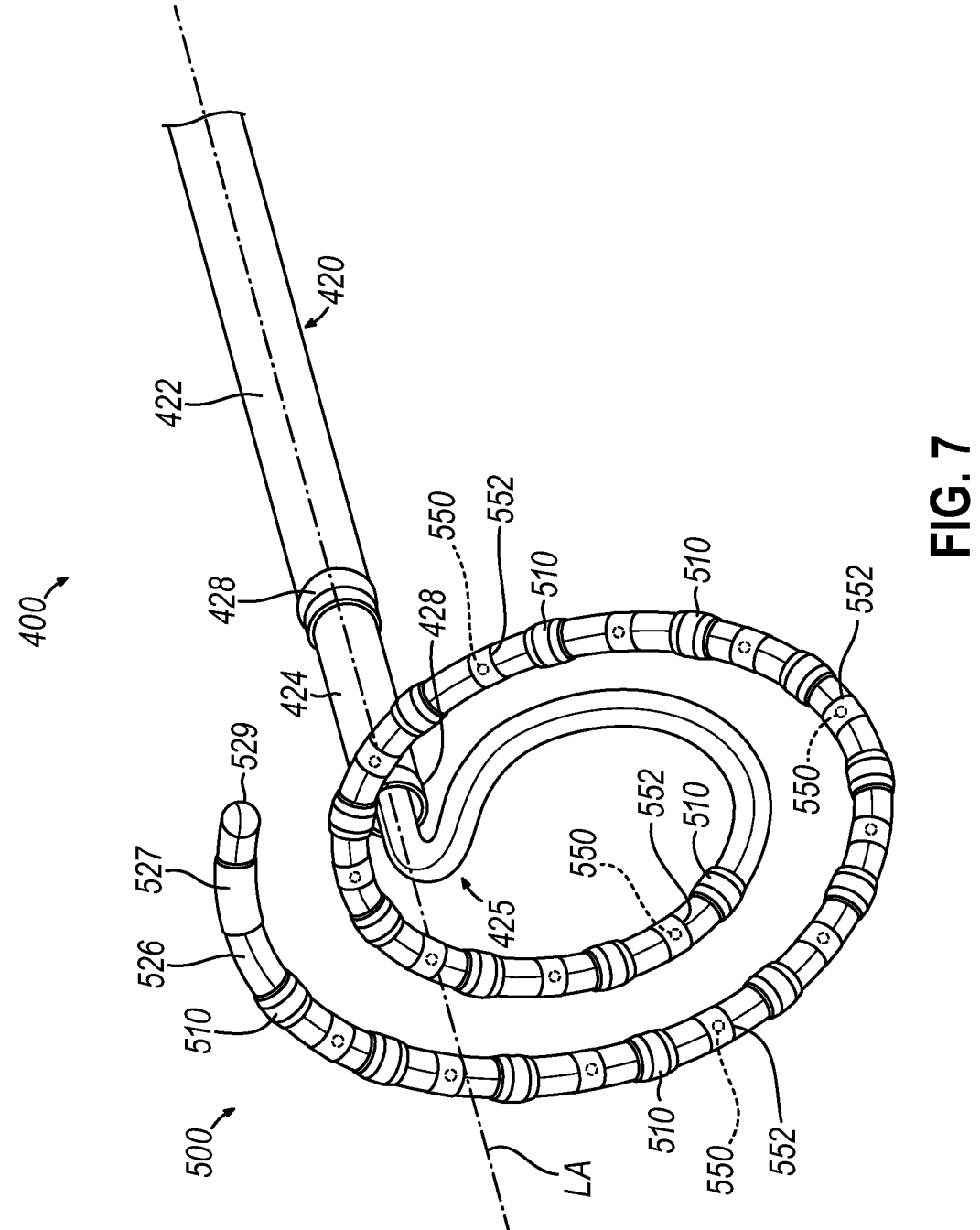
FIG. 7 depicts a perspective view of another example of an end effector for use with the catheter assembly of FIG. 1, with the end effector in an expanded state, and with a plurality of irrigation ports and a plurality of elastic sleeves positioned over corresponding irrigation ports.

As shown in FIG. 7, catheter (420) includes an elongate flexible sheath (422), with end effector (500) being disposed at a distal end (425) of a first inner shaft (424) extending distally from sheath (422). End effector (500) and various components that are contained in sheath (422) will be described in greater detail below. Catheter assembly (400) may be coupled with guidance and drive system (10) via cable (30). Catheter assembly (400) may also be coupled with fluid source (42) via fluid conduit (40).

As also shown in FIG. 7, a pair of active current location (ACL) electrodes (428) are coaxially positioned about shaft (424) for providing position indicative signals to first driver module (14). In some versions, electrodes (428) are configured and operable in accordance with one or more teachings of U.S. Pat. No. 8,456,182, entitled "Current Localization Tracker," issued Jun. 4, 2013, the disclosure of which is incorporated by reference herein. In addition, or alternatively, electrodes (428) may be configured and operable like reference electrodes (128) described above.

In some versions, catheter (420) includes at least one position sensor (not shown), fixedly secured relative to shaft (424), that is operable to generate signals (e.g., in response to the presence of an alternative electromagnetic field generated by magnetic field generators (20)) that are indicative of the position and orientation of shaft (424) within the patient (PA), such as in a manner similar to that described above, in addition to or in lieu of electrodes (428). Such a navigation sensor assembly may be configured as a single-axis sensor (SAS) (e.g., having a single electromagnetic coil wound about a single axis), as a dual-axis sensor (DAS) (e.g., having two electromagnetic coils wound about respective axes), or as a triple-axis sensor (TAS) (e.g., having three electromagnetic coils wound about respective axes). In addition, or alternatively, such a navigation sensor assembly may be configured as a flexible printed circuit board (PCB). By way of example only, such a navigation sensor assembly may be configured and operable in accordance with at least some of the teachings of U.S. patent application Ser. No. 17/584,693, entitled "Flexible Sensor Assembly for ENT Instrument," filed Jan. 26, 2022, the disclosure of which is incorporated by reference herein, in its entirety.

As mentioned above, end effector (500) includes various components configured to provide EP mapping functionality, deliver electrical energy to targeted tissue sites, and/or deliver irrigation fluid. With continuing reference to FIG. 7, end effector (500) of the present version is configured to define a spiral shape when in the expanded shape. By way of example only, end effector (500) may be resiliently biased to assume the spiral shape. In addition, or in the alternative, a drive cable or other actuator may be used to drive end effector (500) toward the spiral shape.

End effector (500) of the example shown in FIG. 7 is mounted to first inner shaft (424), which is internal to outer sheath (422). End effector (500) of this example includes a plurality of ring-shaped ablation electrodes (510) mounted to a second inner shaft (526) of end effector (500), which terminates in a closed distal end (529). Electrodes (510) may each be configured to deliver electrical energy to target tissue. For example, first driver module (14) may be operable to provide electrical energy to electrodes (510) through traces or other electrical conduits via cable (30), to thereby ablate tissue contacting electrodes (510). Such electrical energy may include radiofrequency (AC type) electrical energy, pulsed field (DC type) electrical energy (e.g., irreversible electroporation, etc.), or some other form of electrical energy. In this regard, electrodes (510) may each be formed of an electrically conductive material, such as metal. By way of example only, electrodes (510) may be formed of platinum, gold, or any other suitable material.

In some variations, one or more electrodes (510) may be configured to provide EP mapping rather than tissue ablation. For example, one or more electrodes (510) may be configured to pick up electrical potentials from tissue that comes into contact with such one or more electrodes (510). Such electrodes (510) may thus be used to determine locations of aberrant electrical activity in tissue within a cardiovascular anatomical structure (e.g., pulmonary vein, etc.). Signals picked up by such electrodes (510) may be communicated through traces or other electrical conduits, eventually reaching first driver module (14) of console (12) via cable (30). First driver module (14) may process the EP mapping signals and provide the physician (PH) with corresponding feedback indicating the locations of aberrant electrical activity in accordance with the teachings of various references cited herein. Electrodes (510) may be constructed and operable in accordance with the teachings of various patent references cited herein. In some versions, electrodes (510) may be configured and operable like electrodes (310) described above.

End effector (500) further includes a position sensor (527) located near distal end (529) of second inner shaft (526). Position sensor (527) is operable to generate signals that are indicative of the position and orientation of end effector (500) within the patient (PA). By way of example only, position sensor (527) may be in the form of a wire coil or a plurality of wire coils (e.g., three orthogonal coils) that are configured to generate electrical signals in response to the presence of an alternating electromagnetic field generated by magnetic field generators (20). Position sensor (527) may be coupled with wire, a trace, or any other suitable electrical conduit along or otherwise through catheter (420), thereby enabling signals generated by position sensor (527) to be communicated back through electrical conduits (not shown) in catheter (420) to console (12). Console (12) may process the signals from position sensor (527) to identify the position of end effector (500) within the patient (PA). Other components and techniques that may be used to generate real-time position data associated with end effector (500) may include wireless triangulation, acoustic tracking, optical tracking, inertial tracking, and the like. In some versions, position sensor (527) may be omitted.

As noted above, catheter assembly (400) of the present example is coupled with a fluid source (42) via a fluid conduit (40). A fluid conduit (not shown) extends along the length of catheter (420) and is operable to deliver irrigation fluid (e.g., saline) out through second inner shaft (526). In this regard, end effector (500) of the present version includes a plurality of irrigation ports (550) that extend radially through a sidewall of second inner shaft (526) and are in fluid communication with fluid conduit (40) via the fluid conduit extending along the length of catheter (420). Ports (550) thus allow irrigation fluid to be communicated from fluid source (42) out through second inner shaft (526). As shown, each port (550) may be longitudinally interposed between a corresponding set of electrodes (510), though ports (550) may be provided in any other suitable quantity and/or arrangement. It will be appreciated that the irrigation fluid may provide cooling, flushing, or other effects at end effector (500) during operation of end effector (500) within the patient (PA). For example, the irrigation fluid may provide cooling during performance of an ablation procedure using electrodes (510). Various suitable ways in which catheter assembly (400) may provide irrigation will be apparent to those skilled in the art.

In the example shown, each port (550) is covered by a corresponding sleeve (552) that is configured to transition between a respective closed state (FIG. 9A), in which the sleeve (552) sits tightly against second inner shaft (526) over the corresponding port (550) to inhibit irrigation fluid from flowing radially outwardly through the corresponding port (550); and a respective open state (FIG. 9B), in which at least the portion of the sleeve (552) covering the corresponding port (550) is expanded radially outwardly relative to second inner shaft (526) and thereby tented over the corresponding port (550) to permit irrigation fluid to flow radially outwardly through the corresponding port (550) and between the sleeve (552) and second inner shaft (526) (e.g., toward one or more electrodes (510)). In this regard, each sleeve (552) may include an elastic material, such as an elastomer, such that each sleeve (552) may be resiliently biased toward the respective closed state and may be configured to transition to the respective open state in response to the fluid pressure within second inner shaft (526) reaching a threshold fluid pressure. More particularly, each sleeve (552) of the present example is resiliently biased radially inwardly relative to second inner shaft (526) to assume the respective closed state, and is configured to flex radially outwardly away from the corresponding port (550) toward the respective open state in response to application of a threshold radially outwardly-directed force to the radially inner side of the respective sleeve (552), which may result from the presence of the threshold fluid pressure within second inner shaft (526). For example, each sleeve (552) may be configured to immediately flex toward the respective open state in response to the fluid pressure within second inner shaft (526) reaching the threshold fluid pressure to permit flow of irrigation fluid radially outwardly through the corresponding port (550), and may be configured to immediately resiliently return to the respective closed state in response to the fluid pressure within second inner shaft (526) dropping below the threshold fluid pressure to arrest the flow of irrigation fluid radially outwardly through the corresponding port (550). In this manner, each sleeve (552) may be configured to operate as a self-actuating check valve.

Sleeves (552) may be configured to provide a substantially uniform and/or constant backpressure opposing the flow of fluid through the corresponding ports (550). In this manner, the flow of fluid may be regulated such that the volumetric flow rate or discharge of the fluid may be substantially the same across all ports (550). In addition, or alternatively, the backpressure at each port (550) may not be subject to change based on the particular ambient environment in which end effector (500) is situated, such that the discharge of the fluid through each port (550) may be unaffected by environmental factors such as the fluid media (e.g., air, saline, blood, etc.) in which end effector (500) is situated. Thus, sleeves (552) may cooperate with ports (550) to provide reliable and consistent delivery of irrigation fluid, such as during performance of an ablation procedure using electrodes (510).

As shown in FIGS. 8A-8B, one or more ports (550) may extend through a radially outermost surface of second inner shaft (526), such that the corresponding one or more sleeves (552) may be generally radially outward of the radially outermost surface of second inner shaft (526). In addition, or alternatively, end effector (500) may include one or more radially recessed surfaces (554) disposed radially inwardly of the radially outermost surface of second inner shaft (526), and one or more ports (550) may extend through such radially recessed surfaces (554), such that the corresponding one or more sleeves (552) may be generally flush with the radially outermost surface of second inner shaft (526) (at least when in the closed state). Such a configuration is shown in FIGS. 8C-8D.

In some versions, one or more ports (550) may themselves be configured to transition between a respective closed state and a respective open state. For example, one or more ports (550) may be resiliently biased toward a closed state or substantially closed state in the absence of sufficient fluid pressure within second inner shaft (526); yet may stretch to an open state in response to sufficient fluid pressure within second inner shaft (526). Such ports (550) may thus be configured to self-seal in the absence of the threshold fluid pressure within second inner shaft (526). Such self-sealing functionality may be provided by the material forming inner shaft (526) that defines ports (550). In some such cases, one or more sleeves (552) may be omitted. In either scenario, while not shown in FIG. 7 or 9A-9B, ports (550) may also have aperture size that progressively increases along the length of inner shaft (526), similar to the progressively increasing aperture size of ports (150) shown in FIG. 6. Thus, the aperture size of ports (550) need not necessarily be constant along the length of inner shaft (526). It will be appreciated that the inclusion of resiliently biased sleeves (552) with ports (550) having a fluid bias from progressively increasing aperture size may further promote balanced volumetric flow distribution at both high and low flow rates of the irrigation fluid.

In an example of use of catheter assembly (400), sleeves (552) may initially be in the respective closed states, such as prior to performance of an ablation procedure in or near the heart (H) of the patient (PA) using electrodes (510), as shown in FIG. 9A. When the physician (PH) desires to deliver irrigation fluid out through second inner shaft (526), such as to provide cooling, flushing, or other effects at end effector (500) during operation of end effector (500) within the patient (PA), the fluid pressure within second inner shaft (526) may be increased to the threshold fluid pressure, such as by driving irrigation fluid from fluid source (42) to second inner shaft (526) via pump (44). Each sleeve (552) may then transition to the respective open state in response to the fluid pressure within second inner shaft (526) reaching the threshold fluid pressure to permit irrigation fluid to flow radially outwardly through the corresponding port (550) and between the sleeve (552) and second inner shaft (526) (e.g., toward one or more electrodes (510)), as shown in FIG. 9B, to provide the desired cooling, flushing, or other effects at end effector (500).

After the desired cooling, flushing, or other effects at end effector (500) have been achieved, the fluid pressure within second inner shaft (526) may be reduced to below the threshold fluid pressure, such as by ceasing driving irrigation fluid from fluid source (42) to second inner shaft (526) via pump (44). Each sleeve (552) may then immediately resiliently return to the respective closed state (FIG. 9A) in response to the fluid pressure within second inner shaft (526) dropping below the threshold fluid pressure to arrest the flow of irrigation fluid radially outwardly through the corresponding port (550) and thereby arrest the delivery of irrigation fluid out through second inner shaft (526). This process may be repeated to provide additional cooling, flushing, or other effects at end effector (500). While end effector (500) is shown in the non-expanded state in FIGS. 9A-9B, it will be appreciated that the delivery of irrigation fluid may be performed while end effector (500) is in the expanded state shown in FIG. 7.

III. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a body; (b) a catheter extending distally from the body, the catheter including a lumen; and (c) an end effector extending distally from the catheter, the end effector being operable to dispense fluid, the end effector including: (i) at least one electrode, (ii) at least one port in fluid communication with the lumen of the catheter such that the lumen is operable to communicate the fluid from a fluid source to the at least one port, and (iii) at least one flexible sleeve positioned over the at least one port, the at least one flexible sleeve being configured to transition between a closed state in which the at least one flexible sleeve prevents the fluid from exiting the at least one port, and an open state in which the at least one flexible sleeve permits the fluid to exit the at least one port.

Example 2

The apparatus of Example 1, the at least one flexible sleeve being resiliently biased toward the closed state.

Example 3

The apparatus of any of Examples 1 through 2, the at least one flexible sleeve comprising an elastomer.

Example 4

The apparatus of any of Examples 1 through 3, the at least one flexible sleeve being configured to transition from the closed state to the open state in response to a fluid pressure within the lumen being equal to or greater than a threshold fluid pressure.

Example 5

The apparatus of Example 4, the at least one flexible sleeve being configured to transition from the open state to the closed state in response to the fluid pressure within the lumen being less than the threshold fluid pressure.

Example 6

The apparatus of any of Examples 1 through 5, the at least one port including a plurality of ports.

Example 7

The apparatus of Example 6, the at least one flexible sleeve including a plurality of flexible sleeves.

Example 8

The apparatus of Example 7, each flexible sleeve of the plurality of flexible sleeves being positioned over a corresponding port of the plurality of ports.

Example 9

The apparatus of any of Examples 6 through 8, the at least one electrode including a plurality of electrodes, each port of the plurality of ports being interposed between a corresponding pair of electrodes of the plurality of electrodes.

Example 10

The apparatus of any of Examples 1 through 9, the at least one electrode including at least one ablation electrode configured to deliver electrical energy to tissue.

Example 11

The apparatus of Example 10, the at least one ablation electrode being configured to deliver radiofrequency electrical energy to tissue.

Example 12

The apparatus of any of Examples 10 through 11, the at least one ablation electrode being configured to deliver pulsed field direct current electrical energy to tissue.

Example 13

The apparatus of any of Examples 1 through 12, the at least one electrode including at least one electrophysiology mapping electrode configured to sense potentials in tissue.

Example 14

The apparatus of any of Examples 1 through 13, the end effector being configured to transition between a non-expanded state and an expanded state.

Example 15

The apparatus of Example 14, the end effector being configured to define a spiral shape when the end effector is in the expanded state.

Example 16

An apparatus, comprising: (a) a body; (b) a catheter extending distally from the body, the catheter including a lumen; and (c) an end effector extending distally from the catheter, the end effector being operable to dispense fluid, the end effector including: (i) a plurality of electrodes, (ii) a plurality of ports in fluid communication with the lumen of the catheter such that the lumen is operable to communicate the fluid from a fluid source to each port of the plurality of ports, each port of the plurality of ports being interposed between a corresponding pair of electrodes of the plurality of electrodes, and (iii) a plurality of flexible sleeves, each flexible sleeve of the plurality of flexible sleeves being positioned over a corresponding port of the plurality of ports and being configured to transition between a respective closed state in which the flexible sleeve prevents the fluid from exiting the corresponding port, and an open state in which the flexible sleeve permits the fluid to exit the corresponding port.

Example 17

The apparatus of Example 16, each electrode of the plurality of electrodes including at least one ablation electrode configured to deliver electrical energy to tissue.

Example 18

The apparatus of any of Examples 16 through 17, the end effector being configured to transition between a non-expanded state and an expanded state, the end effector being configured to define a spiral shape when the end effector is in the expanded state.

Example 19

An apparatus, comprising: (a) a body; (b) a catheter extending distally from the body, the catheter including a lumen; and (c) an end effector extending distally from the catheter, the end effector being operable to dispense fluid, the end effector including: (i) at least one electrode, (ii) at least one port in fluid communication with the lumen of the catheter such that the lumen is operable to communicate the fluid from a fluid source to the at least one port, and (iii) at least one flexible sleeve positioned over the at least one port, the at least one flexible sleeve being resiliently biased toward a closed state in which the at least one flexible sleeve prevents the fluid from exiting the at least one port, the at least one flexible sleeve being configured to transition from the closed state to an open state in response to a fluid pressure within the lumen being equal to or greater than a threshold fluid pressure.

Example 20

The apparatus of Example 19, the at least one flexible sleeve being configured to transition from the open state to the closed state in response to the fluid pressure within the lumen being less than the threshold fluid pressure.

IV. Miscellaneous

It should be understood that various modes of energized tissue ablation are possible, including but not limited to RF and IRE (including monopolar or bio-polar high-voltage DC pulses) or combinations may be used depending on need, availability/and/or preference. Accordingly, references herein to "energy" and "generators" herein shall be understood to encompass all such modalities with the scope being determined by the claims herein.

Any of the instruments described herein may be cleaned and sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, hydrogen peroxide, peracetic acid, and vapor phase sterilization, either with or without a gas plasma, or steam.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An apparatus, comprising:
   (a) a body defining a longitudinal axis;
   (b) a catheter extending distally from the body, the catheter including a first shaft with a first lumen; and
   (c) an end effector including a second shaft extending distally from the first lumen of the first shaft, the end effector being operable to dispense fluid, the second shaft configured for longitudinal translation relative to the first shaft such that the end effector is in an expanded state when outside of the first shaft and a non-expanded state when inside of the first shaft, the second shaft of the end effector including a proximal end, a distal end and:

(i) a plurality of electrodes spanning between the proximal end and the distal end, (ii) a plurality of ports in fluid communication with the first lumen of the catheter such that the first lumen is operable to communicate the fluid from a fluid source to each port of the plurality of ports, each port of the plurality of ports being interposed between a corresponding pair of electrodes of the plurality of electrodes, the plurality of ports between the proximal end and the distal end of the second shaft of the end effector having different aperture sizes, and (iii) a plurality of flexible sleeves, each flexible sleeve of the plurality of flexible sleeves being positioned over a corresponding port of the plurality of ports and being configured to transition between a respective closed state in which the flexible sleeve prevents the fluid from exiting the corresponding port, and an open state in which the flexible sleeve permits the fluid to exit the corresponding port.

2. The apparatus of claim 1, at least one of the plurality of flexible sleeves being resiliently biased toward the closed state.

3. The apparatus of claim 1, at least one of the plurality of flexible sleeves comprising an elastomer.

4. The apparatus of claim 1, at least one of the plurality of flexible sleeves being configured to transition from the closed state to the open state in response to a fluid pressure within the first lumen of the catheter being equal to or greater than a threshold fluid pressure.

5. The apparatus of claim 4, at least one of the plurality of flexible sleeves being configured to transition from the open state to the closed state in response to the fluid pressure within the first lumen of the catheter being less than the threshold fluid pressure.

6. The apparatus of claim 1, the plurality of electrodes including at least one electrophysiology mapping electrode configured to sense potentials in tissue.

7. The apparatus of claim 1, the end effector being configured to define a spiral shape when the end effector is in the expanded state.

8. The apparatus of claim 1, each electrode of the plurality of electrodes including at least one ablation electrode configured to deliver electrical energy to tissue.

9. The apparatus of claim 1, the end effector being configured to define a spiral shape when the end effector is in the expanded state.

10. The apparatus of claim 1, further comprising a deflection drive assembly configured to deflect the catheter away from the longitudinal axis.

11. The apparatus of claim 1, further comprising an end effector expansion actuator configured to transition the end effector between the expanded state and the non-expanded state.

12. The apparatus of claim 1, the plurality of ports are configured with aperture sizes that progressively increase along the length of the second shaft of the end effector from the proximal end toward the distal end.

13. The apparatus of claim 1, the plurality of electrodes including at least one ablation electrode configured to deliver electrical energy to tissue.

14. The apparatus of claim 13, the at least one ablation electrode being configured to deliver radiofrequency electrical energy to tissue.

15. The apparatus of claim 13, the at least one ablation electrode being configured to deliver pulsed field direct current electrical energy to tissue.

16. The apparatus of claim 1, the second shaft of the end effector configured with a plurality of radially recessed surfaces, each port extending through a respective radially recessed surface.

17. The apparatus of claim 1, each radially recessed surface configured to receive a respective one of the plurality of flexible sleeves.

18. The apparatus of claim 17, each of the plurality of flexible sleeves being generally flush with an outermost surface of the second shaft of the end effector.

* * * * *